United States Patent [19]

Itoh et al.

[11] Patent Number: 5,177,094

[45] Date of Patent: Jan. 5, 1993

[54] TRIAZOLE COMPOUNDS HAVING ANTIFUNGAL PROPERTIES

[75] Inventors: Katsumi Itoh, Toyono; Kenji Okonogi, Mishima, both of Japan

[73] Assignee: Takeda Chemical Industries, Ltd., Osaka, Japan

[21] Appl. No.: 628,097

[22] Filed: Dec. 14, 1990

[30] Foreign Application Priority Data

Dec. 14, 1989 [JP] Japan .................. 1-325166
Mar. 7, 1990 [JP] Japan .................. 2-056202
May 10, 1990 [JP] Japan .................. 2-122080

[51] Int. Cl.⁵ .................. A01N 43/653; C07D 249/08
[52] U.S. Cl. .................. 514/383; 548/266.6; 548/268.6
[58] Field of Search .................. 548/268.6, 266.6; 514/383

[56] References Cited

U.S. PATENT DOCUMENTS

| | | | |
|---|---|---|---|
| 4,505,919 | 5/1985 | Cooper et al. | 514/340 |
| 4,507,484 | 3/1985 | Gymer et al. | 546/210 |
| 4,678,789 | 7/1987 | Richardson et al. | 514/262 |

FOREIGN PATENT DOCUMENTS

| | | |
|---|---|---|
| 0061835 | 10/1982 | European Pat. Off. . |
| 100193 | 2/1984 | European Pat. Off. . |
| 0178533 | 4/1986 | European Pat. Off. . |
| 0332387 | 9/1989 | European Pat. Off. . |

Primary Examiner—Patricia L. Morris
Attorney, Agent, or Firm—Wegner, Cantor, Mueller & Player

[57] ABSTRACT

The novel azole compounds of the formula:

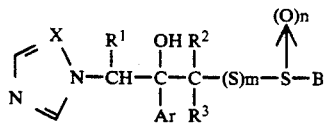

wherein Ar stands for substituted phenyl; $R^1$, $R^2$ and $R^3$ independently stand for a hydrogen atom or a lower alkyl group; B stands for a hydroxyl group or an organic residue bonded through a carbon atom; X stands for a CH group or a nitrogen atom; m denotes an integer of 1 to 4; n denotes an integer of 0 to 2, provided that, when B is a hydroxyl group, n is 2, or a physiologically acceptable salt thereof have antifungal activities, and they are used preventing or treating infectious diseases caused by fungi.

22 Claims, No Drawings

TRIAZOLE COMPOUNDS HAVING ANTIFUNGAL PROPERTIES

FIELD OF THE INVENTION

This invention relates to azole compounds, their production and use. The said compounds are useful as antifungal agents or the intermediate for their synthesis, being useful in the field of drugs and agricultural chemicals.

BACKGROUND OF THE INVENTION

Various compounds have been reported as antifungal agents.

For example, triazole derivatives were disclosed as compounds having antifungal activities in the Gazette of Japanese Unexamined Patent Publication No. 189173/83 and No. 98072/84. However, it is difficult to say that these compounds are effective enough as drugs from the standpoints of their antifungal activity, side effect, and absorption.

Conventional antifungal therapeutics are not sufficiently effective, having various problems such as occurrence of side effects, replacement of fungus, and resistance.

To solve such problems, compounds having higher safety and more potent antifungal activities have been desired as antifungal therapeutics.

SUMMARY OF THE INVENTION

This invention relates to:
1. A compound represented by the general formula (I):

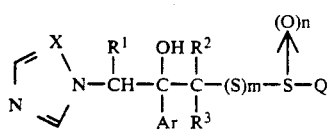

[wherein Ar stands for a substituted phenyl group; $R^1$, $R^2$ and $R^3$ independently stand for a hydrogen atom or a lower alkyl group; Q stands for a hydroxyl group or an organic residue bonded through a carbon atom; X stands for a CH group or a nitrogen atom; m denotes an integer of 1 to 4; n denotes an integer of 0 to 2, provided that, when Q is a hydroxyl group, n is 2], or a physiologically acceptable salt thereof.

2. A method for producing a compound of the formula (I)

3. An antifungal agent containing a compound of the formula (I).

DETAILED DESCRIPTION OF THE INVENTION

This invention provides:
1. A compound represented by the general formula (I):

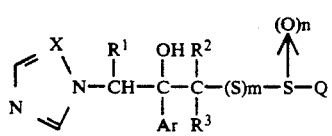

wherein Ar stands for a substituted phenyl group; $R^1$, $R^2$ and $R^3$ independently stand for a hydrogen atom or a lower alkyl group; Q stands for a hydroxyl group or an organic residue bonded through a carbon atom; X stands for a CH group or a nitrogen atom; m denotes an integer of 1 to 4; n denotes an integer of 0 to 2, provided that, when Q is a hydroxyl group, n is 2, or a physiologically acceptable salt thereof.

2. A method for producing a compound of the formula (I).

3. An antifungal agent containing a compound of the formula (I).

Referring to the compound (I), the substituted phenyl group shown by Ar is a phenyl group having 1 to 3 substituents independently selected from halogen and trifluoromethyl, as exemplified by 2,4-difluorophenyl, 2,4-dichlorophenyl, 4-fluorophenyl, 4-chlorophenyl, 4-trifluoromethylphenyl, 2-fluoro-4-chlorophenyl, 2-chloro-4-fluorophenyl, 4-bromophenyl and 2,4,6-trifluorophenyl. Especially, 2,4-difluorophenyl is preferable as Ar.

Referring to the compound (I), the lower alkyl group, shown by $R^1$, $R^2$ or $R^3$, is exemplified by straight-chain or branched $C_{1-3}$ alkyl such as methyl, ethyl, propyl, isopropyl etc., or the lower alkylene group which is formed by combination of $R^2$ and $R^3$, such as ethylene and propylene, etc. Especially when $R^1$ is a hydrogen atom, $R^2$ is preferably a hydrogen atom and $R^3$ is preferably methyl.

Referring to the compound (I), examples of the organic residue, shown by Q, bonded through a carbon atom include an aliphatic chain hydrocarbon residue such as alkyl, alkenyl, alkynyl, etc., aliphatic cyclic hydrocarbon residue such as cycloalkyl group and cycloalkenyl group, aryl group, aralkyl group, etc., heterocyclic group, a group represented by the formula:

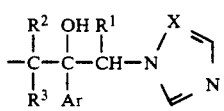

(wherein $R^1$, $R^2$, $R^3$, Ar and X are of the same meaning as defined above) and a group represented by the formula:

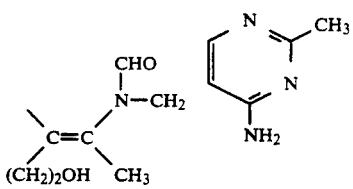

As the alkyl group, mention is made of those having 1 to 12 carbon atoms, which are exemplified by methyl, ethyl, propyl, butyl, heptyl, octyl, nonyl, decyl, dodecyl, etc., and these alkyl groups may be straight-chain or branched ones.

As the alkenyl groups, mention is made of those having 2 to 6 carbon atoms, which are exemplified by allyl, vinyl, 1,3-butadienyl, 2,4-pentadienyl, 1,3,5-hexatrienyl, isoprenyl, etc.

As the alkynyl, mention is made of those having 2 to 6 carbon atoms, which are exemplified by ethynyl, 1-propinyl, 1-pentynyl, etc.

Examples of the aryl include phenyl, naphthyl, biphenyl, anthryl, indenyl, etc.

As the aralkyl, mention is made of preferably phenyl($C_{1-4}$)alkyl, which is exemplified by benzyl, phenethyl, phenylpropyl, etc.

As the cycloalkyl, mention is made of preferably those having 3 to 7 carbon atoms, as exemplified by cyclopropyl, cyclobutyl, cyclopentyl, cyclohexyl, cycloheptyl, etc.

As the cycloalkenyl groups, mention is made of preferably those having 5 to 7 carbon atoms, as exemplified by cyclopentenyl, cyclohexenyl, cycloheptenyl, etc.

As the heterocyclic group, mention is made of aromatic or non-aromatic 5- to 6-membered ones, as exemplified by imidazolyl, triazolyl, pyrazolyl, pyridyl, thiazolyl, thienyl, furyl, tetrahydrofuryl, pyrrolyl, pyrazinyl, pyrimidyl, isoxazolyl, oxazolyl, tetrazolyl, piperazinyl, morpholinyl, piperidyl, etc. The heterocyclic group may further optionally be condensed with a 5- to 7-membered ring, as exemplified by benzimidazolyl, imidazopyrimidinyl, imidazopyridinyl, imidazopyrazinyl, imidazopyridazinyl, benzothiazolyl, indolyl, isoquinolyl, quinolyl, phthalazinyl, quinazolyl, cinnolyl, etc.

In the above-mentioned formula (I), the organic residue, shown by Q, bonded through a carbon atom, may have 1 to 3 of the same or different substituents. Examples of those substituents include a hydroxyl group, optionally esterified carboxyl group (e.g.: carboxy, ethoxycarbonyl, methoxycarbonyl, butoxycarbonyl), amidated carboxyl group (e.g.: carbamoyl, dimethylaminocarbonyl, diethylaminocarbonyl, morpholinocarbonyl, piperidinocarbonyl), carboxy group peptide-bonded with an amino acid (e.g.: glycinocarbonyl, alaninocarbonyl, argininocarbonyl, cysteinocarbonyl, tryptophanocarbonyl, aspartocarbonyl, asparaginocarbonyl, glutamocarbonyl, histidinocarbonyl, leucinocarbonyl, isoleucinocarbonyl, $N^\alpha$-lysinocarbonyl, $N^\epsilon$-lysinocarbonyl, methioninocarbonyl, norleucinocarbonyl, norvalinocarbonyl, $N^\alpha$-ornithinocarbonyl, $N^\epsilon$-ornithinocarbonyl, prolinocarbonyl, sarcosinocarbonyl, serinocarbonyl, threoninocarbonyl, tyrosinocarbonyl, valinocarbonyl), carboxyl group peptide-bonded with a peptide constituted with two or more amino acids (e.g.: glycinoglycinocarbonyl, alaninoglycinocarbonyl), amino group, acylamino group (e.g.: acetylamino, propionylamino, butyrylamino), amino group peptide-bonded with amino acid (e.g.: glycylamino, alanylamino, arginylamino, cysteinylamino, tryptophylamino, $\alpha$-aspartylamino, $\beta$-aspartylamino, asparaginylamino, $\alpha$-glutamylamino, $\beta$-glutamylamino, glutaminylamino, histidylamino, leucylamino, isoleucylamino, lysylamino, methionylamino, norleucylamino, norvalylamino, ornithylamino, prolylamino, sarcosylamino, serylamino, threonylamino, tyrosylamino, valylamino), amino group peptide-bonded with two or more amino acids (e.g.: glycylglycylamino, alanylglycylamino), alkylamino group (e.g.: methylamino, dimethylamino, diethylamino dibutylamino), alkoxy group (e.g.: methoxy, ethoxy, butoxy), halogen (e.g.: fluoro, chloro, bromo), oxo, thioxo, mercapto, alkylthio group (e.g.: methylthio, ethylthio, butylthio) and cyano, and further include alkyl, alkenyl, alkynyl, aryl, aralkyl, cycloalkyl, heterocyclic group,.etc. exemplified by organic residues shown for Q.

The integral number m is preferably 1 or 2.

In the above-mentioned formula (I), when B is a hydroxyl group, m is 1 and n is 2, the compound is preferably a salt (usually called "Bunte salt") formed with an alkali metal.

The compounds of the present invention are disclosed concretely, as exemplified in Table 1-1 and Table 1-2.

TABLE 1-1

| Compd. No. | Configuration C* | Configuration C** | A |
|---|---|---|---|
| 1 | (RS) | (RS) | —SCH$_2$—furanyl(O) |
| 2 | (R) | (R) | —SCH$_2$—furanyl(O) |
| 3 | (RS) | (RS) | —SCH$_2$CH$_2$OH |
| 4 | (R) | (R) | —SCH$_2$CH$_2$OH |
| 5 | (RS) | (RS) | (R) —SCH$_2$—CH(NHCOCH$_3$)—COOC$_2$H$_5$ |

TABLE 1-1-continued

[Structure: Triazole-NCH₂-C*(OH)(2,4-difluorophenyl)-C**H(CH₃)-S-A]

| Compd. No. | Configuration C* | Configuration C** | A |
|---|---|---|---|
| 6 | (R) | (R) | —SCH₂—CH(R)(NHC(=O)CH₃)—COOC₂H₅ |
| 7 | (RS) | (RS) | —SCH₂—CH(R)(NHC(=O)CH₃)—COOH |
| 8 | (R) | (R) | —SCH₂—CH(R)(NHC(=O)CH₃)—COOH |
| 9 | (RS) | (RS) | —SCH₂CH(OH)CH₂OH |
| 10 | (R) | (R) | —SCH₂CH(OH)CH₂OH |
| 11 | (RS) | (RS) | —SCH₂CH₂NHC(=O)CH₃ |
| 12 | (R) | (R) | —SCH₂CH₂NHC(=O)CH₃ |
| 13 | (RS) | (RS) | —S(CH₂)₂—CH(NHC(=O)CH₃)—COOC₂H₅ |
| 14 | (R) | (R) | —S(CH₂)₂—CH(NHC(=O)CH₃)—COOC₂H₅ |
| 15 | (RS) | (RS) | —SCH(CH₃)—C(OH)(2,4-difluorophenyl)—CH₂—N(triazole) |

TABLE 1-1-continued

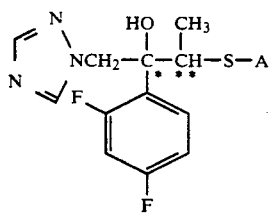

| Compd. No. | Configuration C* | Configuration C** | A |
|---|---|---|---|
| 16 | (R) | (R) | -SCH(CH₃)-C(OH)(R)-CH₂-N(triazole) on 2,4-difluorophenyl (R) |
| 17 | (RS) | (RS) | -SCH₂CH(NH₂)COOH (R) |
| 18 | (R) | (R) | -SCH₂CH(NH₂)COOH (R) |
| 19 | (RS) | (RS) | -SCH₂CH(NH₂)COOC₂H₅ (R) |
| 20 | (R) | (R) | -SCH₂CH(NH₂)COOC₂H₅ (R) |
| 21 | (RS) | (RS) | -SCOOC₂H₅ |
| 22 | (R) | (R) | -SCOOC₂H₅ |
| 23 | (RS) | (RS) | -S-C(=C(CH₃)-N(CHO)-CH₂-(4-amino-2-methylpyrimidin-5-yl))-(CH₂)₂OH |
| 24 | (R) | (R) | -S-C(=C(CH₃)-N(CHO)-CH₂-(4-amino-2-methylpyrimidin-5-yl))-(CH₂)₂OH |
| 25 | (RS) | (RS) | -SCH₂-(furan-2-yl) |
| 26 | (R) | (R) | -SCH₂-(furan-2-yl) |
| 27 | (RS) | (RS) | -SCH₂CH₂N(CH₃)₂ |
| 28 | (R) | (R) | -SCH₂CH₂N(CH₃)₂ |

TABLE 1-1-continued
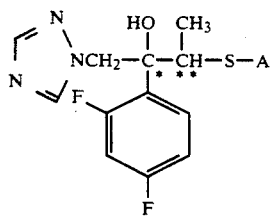
| Compd. No. | Configuration C* | Configuration C** | A |
|---|---|---|---|
| 29 | (R) | (R) | -S-S-CH(R)(CH3)-C(R)(OH)-CH2-N(triazolyl)-2,4-difluorophenyl |
| 30 | (R) | (R) | -SSS-CH(R)(CH3)-C(R)(OH)-CH2-N(triazolyl)-2,4-difluorophenyl |
| 31 | (R) | (R) | -SO-CH(R)(CH3)-C(R)(OH)-CH2-N(triazolyl)-2,4-difluorophenyl |
| 32 | (R) | (R) | -SO2-CH(R)(CH3)-C(R)(OH)-CH2-N(triazolyl)-2,4-difluorophenyl |
| 33 | (RS) | (RS) | -SCH2CH(R)C(O)NHCH2COOH, HNCCH2CH2CH(S)COOH / NH2 (with C=O) |
| 34 | (R) | (R) | -SCH2CH(R)C(O)NHCH2COOH, HNCCH2CH2CH(S)COOH / NH2 (with C=O) |

TABLE 1-1-continued

[Structure: triazole-N-CH₂-C*(OH)(Ar)-C**H(CH₃)-S-A, where Ar = 2,4-difluorophenyl]

| Compd. No. | Configuration C* | Configuration C** | A |
|---|---|---|---|
| 35 | (RS) | (RS) | -S-C(CH₃)₂-CH(S)(NH₂)-COOH |
| 36 | (R) | (R) | -S-C(CH₃)₂-CH(S)(NH₂)-COOH |
| 37 | (RS) | (RS) | -S-CH₂-CH=CH₂ |
| 38 | (R) | (R) | -S-CH₂-CH=CH₂ |
| 39 | (R) | (R) | -S-C(=S)-N(C₂H₅)₂ |
| 40 | (R) | (R) | -S-CH₂-(N-methylimidazol-2-yl) |
| 41 | (R) | (R) | -S-CH(CH₃)CONHCH₂COOH |

TABLE 1-2

| Compd. No. | |
|---|---|
| 42 | [Disulfide dimer structure with cyclopropyl groups, HO, triazolyl-CH₂, and 2,4-difluorophenyl groups] |
| 43 | [Disulfide dimer with gem-dimethyl groups, HO, triazolyl-CH₂, and 2,4-difluorophenyl groups] |
| 44 | [Disulfide dimer (R,R,R,R) with CH₃, HO, imidazolyl-CH₂, and 2,4-difluorophenyl groups] |

The compound (I) has, in its molecule, one or more asymmetric atoms, and the stereoisomer with R-configuration, the stereoisomer with S-configuration and a mixture thereof are all included in the present invention. Especially, when R¹ and R² are hydrogen, and when R³ is methyl, both the carbon bonded to the hydroxyl and Ar groups and the carbon bonded to R³ are preferably of R-configuration.

The compound (I) can be obtained also as a salt. The salt is exemplified by inorganic acid salts such as hydrochloride, hydrobromide, sulfate, nitrate, phosphate, etc., organic acid salts such as acetate, tartrate, citrate, fumarate, maleate, toluenesulfonate, methanesulfonate, etc., metal salts such as sodium salt, potassium salt, calcium salt, aluminum salt, etc., and salts with a base, such as triethylamine salt, guanidine salt, ammonium salt, hydrazine salt, quinine salt, cinchonine salt, etc.

A compound (I), wherein m is 1, n is 0 and Q is an organic residue bonded through a carbon atom, can be prepared by allowing a compound represented by the formula,

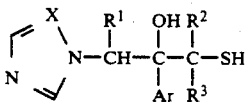 (II)

[wherein the symbols are of the same meaning as defined above] to react with a compound represented by the general formula,

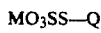 (III)

[wherein Q' is an organic residue bonded through a carbon atom, and M stands for an alkali metal (e.g. sodium, potassium)]. The reaction can be allowed to proceed usually in the presence or absence of water or an organic solvent (e.g. methanol, ethanol, butanol, propanol, dimethylsulfoxide, dimethylformamide) singly or a mixture thereof, while keeping the temperature at a range from about $-20°$ C. to about $+100°$ C. In this case, for accelerating the reaction rate, a base such as potassium carbonate, potassium hydroxide, sodium carbonate, sodium hydroxide, sodium methylate, etc. can be allowed to coexist in the reaction system.

A compound (I), wherein m is 1, n is 0 and Q is an organic residue bonded through a carbon atom, can be prepared by allowing a compound of the formula,

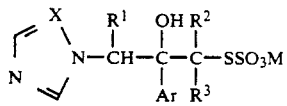 (IV)

[wherein the symbols are of the same meaning as defined above] to react with a compound of the general formula,

 (V)

[wherein Q' is of the same meaning as defined above. The reaction can usually be allowed to proceed in the presence or absence of water or an organic solvent (e.g. methanol, butanol, propanol, dimethylsulfoxide and dimethylformamide) singly or in a mixture thereof, while keeping the temperature in a range from about $-20°$ C. to about $+100°$ C. In this case, for accelerating the reaction rate, a base such as potassium carbonate, potassium hydroxide, sodium carbonate, sodium hydroxide, sodium methylate, etc. may be allowed to coexist in the reaction system.

And, a compound (I), wherein m is 1, n is 0 and Q is

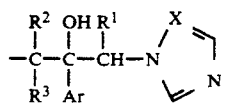

can be produced by, for example, subjecting a compound represented by the formula,

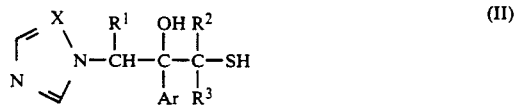 (II)

[wherein $R^1$, $R^2$, $R^3$, Ar and X are of the same meaning as defined above] or a metal salt thereof (e.g. sodium salt, potassium salt, lead salt, etc.) to oxidation.

The above reaction can usually be allowed to proceed by using an oxidizing agent (e.g. hydrogen peroxide, lead dioxide, potassium permanganate, potassium ferricyanide, sulfuryl chloride, iodine, oxygen, ammonium persulfate, bromine, dimethyl sulfoxide, sulfur dioxide, nitrogen oxide, phosphorus pentachloride, copper sulfate, etc.) in water or an organic solvent (e.g. methylene chloride, chloroform, acetone, ethyl acetate, dioxane, tetrahydrofuran, acetonitrile, methanol, ethanol) singly or in a mixture thereof at temperatures ranging from $-20°$ C. to $100°$ C. In this case, for accelerating the reaction rate, a base such as potassium carbonate, sodium hydroxide, triethylamine, polyvinyl pyridine, pyridine, etc. may be allowed to coexist in the reaction system.

And, a compound (I), wherein m is 1, n is 0 and Q is

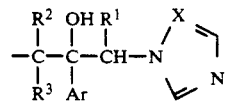

can be produced by, for example, subjecting a compound represented by the formula,

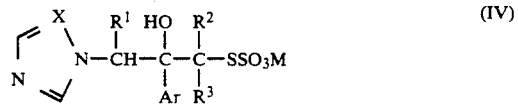 (IV)

[wherein $R^1$, $R^2$, $R^3$, Ar, X and M are of the same meaning as defined above] to oxidation.

The above reaction can usually be allowed to proceed by using an oxidizing agent (e.g. hydrogen peroxide, lead dioxide, potassium permanganate, potassium ferricyanide, sulfuryl chloride, iodine, oxygen, ammonium persulfate, bromine, dimethyl sulfoxide, sulfur dioxide, nitrogen oxide, phosphorus pentachloride, copper sulfate, etc.) in water or an organic solvent (e.g. methylene chloride, chloroform, acetone, ethyl acetate, dioxane, tetrahydrofuran, acetonitrile, methanol, ethanol) singly or in a mixture thereof at temperatures ranging from $-20°$ C. to $100°$ C. In this case, for accelerating the reaction rate, a base such as potassium carbonate, sodium hydroxide, triethylamine, polyvinyl pyridine, pyridine, etc. may be allowed to coexist in the reaction system.

Further, a compound (I), wherein m is 1, n is 0 and Q is

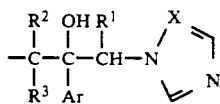

can be produced by, for example, allowing a compound represented by the formula

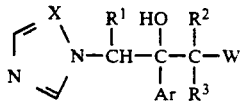  (VI)

[wherein $R^1$, $R^2$, $R^3$, Ar and X are of the same meaning as defined above, and W stands for halogen or a group shown by $R^4$—$SO_2$—O— (wherein $R^4$ stands for lower ($C_{1-4}$) alkyl, trifluoromethyl, phenyl or p-tolyl)] to react with a compound represented by the formula, $$M_2'—S_2 \quad (VII)$$

[wherein M' stands for sodium, potassium, lithium].

The above reaction can usually be allowed to proceed in water or an organic solvent (e.g. methylene chloride, chloroform, acetone, ethyl acetate, dioxane, tetrahydrofuran, acetonitrile, methanol, ethanol) singly or in a mixture thereof at temperatures ranging from $-20°$ C. to $100°$ C.

And, a compound (I), wherein m is 1, n is 0 and Q is an organic residue bonding through a carbon atom, can be produced by, for example, allowing a compound represented by the formula (II) to react with a compound represented by the general formula,

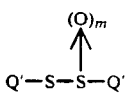  (VIII)

[wherein m denotes an integer of 1-2, and Q' is of the same meaning as defined above]. The reaction can be allowed to proceed usually by keeping the reaction system at temperatures ranging from about $-20°$ C. to about $+100°$ C. in the presence of water or an organic solvent (e.g. methanol, ethanol, acetic acid, butanol, propanol, dimethyl sulfoxide, dimethylformamide, methylene chloride, ethyl acetate, dioxane, tetrahydrofuran, acetonitrile, acetone, chloroform) singly or in a mixture thereof. In this case, for accelerating the reaction rate, a base such as potassium carbonate, potassium hydroxide, sodium carbonate, sodium hydroxide or sodium methylate can be allowed to coexist in the reaction system. The starting compound (VIII) can be obtained by, for example, subjecting a compound represented by the general formula, $$Q'—S—S—Q' \quad (IX)$$

[wherein the symbols are of the same meaning as defined above] to oxidation. In this case, (VIII) thus produced may be reacted with (II), after isolation, or without isolation from the reaction mixture.

And, the compound (I), wherein m is 1, n is 0 and Q is an organic residue bonding through a carbon atom, can be produced by allowing a compound represented by the formula (II) to react with a compound represented by the general formula, $$X—S—Q' \quad (X)$$

[wherein X stands for halogen (e.g. chlorine, bromine, iodine), NCS—, $R^4O_2CS$— (wherein $R^4$ stands for a lower alkyl group),

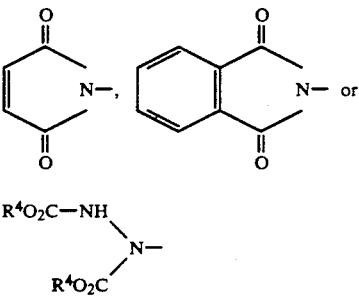

(wherein $R^4$ is of the same meaning as defined above), and Q' is of the same meaning as defined above]. The reaction can be allowed to proceed usually by keeping the reaction system at temperatures ranging from about $-20°$ C. to about $100°$ C. in the presence of water or an organic solvent (e.g. methanol, ethanol, ethyl acetate, benzene, toluene, ethyl ether, tetrahydrofuran, acetone, methylene chloride, dimethylformamide, dimethyl sulfoxide) singly or a mixture thereof. In this case, for accelerating the reaction rate, a base such as pyridine, triethylamine, etc. can be allowed to coexist in the reaction system.

And, the compound (I), wherein m is 1, n is 0 and Q is an organic residue bonding through a carbon atom, can be produced by, for example, allowing a compound represented by the formula (V) to react with a compound represented by the formula,

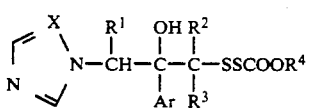  (XI)

wherein $R^1$, $R^2$, $R^3$, $R^4$, X and Ar are of the same meaning as defined above]. The reaction can be allowed to proceed usually by keeping the reaction system at temperatures ranging from about $-20°$ C. to about $100°$ C. in the presence of water or an organic solvent (e.g. methanol, ethanol, ethyl acetate, benzene, toluene, ethyl ether, tetrahydrofuran, acetone, methylene chloride, dimethylformamide, dimethyl sulfoxide) singly or in a mixture thereof. In this case, for accelerating the reaction rate, a base such as pyridine, triethylamine, etc. can be allowed to coexist in the reaction system.

And, a compound (I), wherein m is 2 to 4, n is 0 and Q is

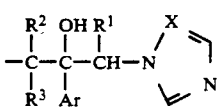

can be produced by subjecting a compound represented by the formula (XI) to the treatment with a base (e.g. potassium tert-butoxide, sodium methoxide, sodium ethoxide, etc.). The reaction can be allowed to proceed usually by keeping the reaction system at temperatures ranging from about −40° C. to about +100° C. in water or an organic solvent (e.g. methanol, ethanol, isopropanol, tetrahydrofuran, dioxane, dimethyl sulfoxide, etc.) singly or in a mixture thereof.

And, a compound (I), wherein m is 2, n is 0 and Q is

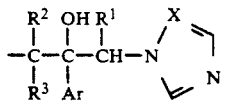

can be produced by allowing a compound represented by the formula (II) to react with a compound represented by the formula, $$X'-S-X' \qquad (XII)$$

[wherein X' stands for halogen (e.g. chlorine, bromine, iodine)]. The reaction can be allowed to proceed usually by keeping the reaction system at temperatures ranging from about −20° C. to about +100° C. in an organic solvent (e.g. carbon disulfide, petroleum ether, methylene chloride, chloroform, isopropyl ether, benzene, toluene, dimethyl sulfoxide, dimethylformamide, etc.). In this case, for accelerating the reaction rate, it is also possible that a base (e.g. triethylamine, pyridine, sodium carbonate, potassium carbonate, sodium hydrogencarbonate, etc.) is allowed to coexist in the reaction system.

And, a compound (I), wherein m is 1, n is 1 to 2 and Q is

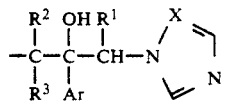

can be produced by subjecting a compound represented by the formula

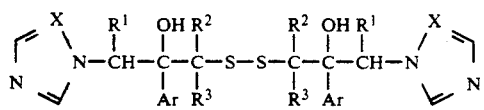

(XIII)

[wherein symbols are of the same meaning as defined above] to oxidation. The reaction can be allowed to proceed usually by allowing an oxidizing agent (e.g. m-chloroperbenzoic acid, peracetic acid, hydrogen peroxide, benzoyl peroxide) to act at temperatures ranging from −20° C. to 50° C. in water or an organic solvent (e.g. methylene chloride, chloroform, isopropyl alcohol, benzene, acetic acid, ethyl acetate, toluene) singly or as a mixture thereof, and, as the oxidizing agent, m-chloroperbenzoic acid is preferable. In this oxidation reaction, by controlling the equivalency of an oxidizing agent relative to the compound (XIII), a compound (I), wherein n is 1 or 2, can be obtained singly or as the mixture thereof. And, also by controlling the reaction temperatures or reaction time, a compound (I), wherein n is 1 or 2, can be obtained singly or as the mixture thereof.

And, a compound (I), wherein m is 1, n is 0 and Q

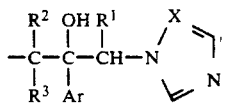

can be obtained by subjecting a compound represented by the formula (II) or a metal salt thereof (e.g. sodium salt, potassium salt, etc.) to treatment with a compound represented by the formula, $$R^4-SO_2-X' \qquad (XIV)$$

[wherein $R^4$ and X' are of the same meaning as defined above]. The reaction can be allowed to proceed usually by keeping the reaction system at temperatures ranging from about −80° C. to about 100° C. in an organic solvent (e.g. ethyl acetate, acetone, methylene chloride, tetrahydrofuran, benzene, toluene, etc.). In this case, for accelerating the reaction rate, a base such as pyridine, triethylamine, etc. may be allowed to coexist in the reaction system.

The resulting compound (I) can be isolated from the reaction mixture by a conventional purification procedure such as extraction, concentration, neutralization, filtration, recrystallization, column chromatography and thin-layer chromatography.

The compound (I) may exist as at least two stereoisomers. These isomers as well as a mixture thereof are subsumed in the concept of the present invention and, if desired, can be produced individually. For example, by subjecting a single isomer of the starting compound (II), (III), (IV), (V), (VI), (VIII), (IX), (X), (XI), (XIII) or (XIV) to the corresponding reaction described hereinbefore, the corresponding isomer of the compound (I) can be selectively produced. On the other hand, when the reaction product is a mixture of two or more isomers, it can be fractionated into respective isomers by conventional resolution or fractionation techniques such as formation of a salt with an optically active acid (e.g. camphorsulfonic acid, tartaric acid, etc.), several types of chromatography, fractional recrystallization and so on.

A physiologically acceptable salt of the compound (I) can be produced by adding one of the aforementioned inorganic acids or organic acids.

Effects

The antifungal activities (in vivo) of the compound (I) were evaluated by the following method.

Test Method: Five-week-old $Crj:CDF_1$ mice were inoculated with the minimum lethal dose of Candida albicans intravenously. The test drug was given once 0 hour after infection or twice after 0 hour and 2 hours after infection. The efficacy of the drug was expressed in $ED_{50}$ values calculated by the Reed and Muench method from the survival rate on day 7 after infection. The $ED_{50}$ values were calculated based on the total dose given. The protective effects of the compounds (I) against experimental murine candidosis were shown in Table 2.

TABLE 2

| Compd. | ED50 (mg/kg) | |
|---|---|---|
| No. | Given twice | Given once |
| 1 | 0.50(S.C.) | — |
| 15 | 0.39(S.C.) | — |

TABLE 2-continued

| Compd. No. | ED50 (mg/kg) Given twice | Given once |
|---|---|---|
| 16 | 0.18(S.C.), 0.18(P.O.) | 0.18(S.C.), 0.18(P.O.) |
| 2 | 0.71(S.C.) | — |
| 4 | 0.18(S.C.), 0.35(P.O.) | — |
| 6 | — | 0.50(P.O.) |
| 10 | — | 0.50(P.O.) |
| 12 | 0.13(S.C.), 0.35(P.O.) | — |
| 22 | — | 0.50(P.O.) |
| 24 | — | 0.50(P.O.) |
| 28 | — | 0.50(P.O.) |
| 29 | — | 0.35(P.O.) |
| 30 | — | 0.50(P.O.) |
| 18 | — | 0.18(P.O.) |
| 34 | — | 0.50(P.O.) |
| 31 | — | 0.50(P.O.) |
| 32 | — | 0.50(P.O.) |
| 36 | — | 0.50(P.O.) |
| 39 | — | 0.50(P.O.) |
| 40 | — | <0.25(P.O.) |
| 41 | — | 0.088(P.O.) |
| 42 | — | 0.77(P.O.) |
| 43 | — | 0.70(P.O.) |
| 44 | — | >4.0(P.O.) |

S.C.: subcutaneous administration
P.O.: oral administration

The antifungal activities (in vitro) were measured by the following method: a sheet of filter paper disc (manufactured by Toyo Seisakusho, 8 mm in diameter) soaked in a 1000 μg/ml solution of a compound (I) in methanol was placed on an agar plate, which was incubated at 28° C. for 2 days, and the diameter of the growth inhibition zone around the filter paper disc was measured. The following culture media were used:

a. yeast nitrogen base agar medium (pH 7.0)
b. Sabouraud agar medium

The antifungal spectra of the compounds (I) are shown in Table 3.

TABLE 3

| | Antifungal Spectra | | |
|---|---|---|---|
| | | Growth-inhibition (mm) | |
| Test fungi | Media | Compound 15 | Compound 16 |
| Candida albicans IFO 0583 | a | 30 | 30 |
| Candida utilis IFO 0619 | a | 27 | 23 |
| Cryptococcus neoformans IFO 0410 | a | 22 | 15 |
| Tricophyton rubrum IFO 6467 | b | 14 | 15 |

The antifungal activities of the compound (I) against *Candida albicans* were shown in Table 4.

TABLE 4

| Compd. No. | Growth-inhibition zone diameter (mm) Candida albicans (IFO 0583) (Medium a) |
|---|---|
| 1 | 45 |
| 2 | 40 |
| 4 | 43 |
| 6 | 22 |
| 8 | 25 |
| 12 | 30 |
| 18 | 21 |
| 22 | 17 |
| 24 | 16 |
| 28 | 25 |
| 29 | 20 |
| 30 | 16 |
| 31 | 30 |
| 32 | 23 |
| 34 | 20 |

TABLE 4-continued

| Compd. No. | Growth-inhibition zone diameter (mm) Candida albicans (IFO 0583) (Medium a) |
|---|---|
| 36 | 16 |
| 39 | 18 |
| 40 | 35 |
| 41 | 18 |
| 42 | 25 |
| 43 | 23 |
| 44 | 15 |

The compounds of this invention, having low toxicities and high antifungal activities with broad antifungal spectra as shown above, can be used for prevention and treatment of fungal infections in man, domestic animals and fowls.

And, the compounds of this invention can also be used as antifungal preparations for agricultural use. The compounds represented by the formula (II), which are intermediates for producing the compounds of this invention, have also antifungal activities. When the compounds are given to man, the compounds can be given safely orally or parenterally, as they are or in the form of pharmaceutical compositions such as powders, granules, tablets, capsules, and injections produced by mixing with appropriate pharmaceutically acceptable carriers, excipients, or diluents. The dose may vary with conditions of infection and the route of administration; for example the oral dose for treatment of candida infection for an adult is 0.1 to 100 mg/kg/day, desirably 1 to 50 mg/kg/day.

The compounds of this invention can be used also as an antifungal preparation for external application. For example, skin or mucosa membrane can be sterilized and disinfected by applying a compound of this invention as an ointment containing usually 0.1 to 100 mg of the compound per gram of the preparation, using, for example, vaseline or hydrous lanolin as the base.

EXAMPLES

Example 1

To dichloromethane (20 ml) was added (2RS,3RS)-2(2,4-difluorophenyl)-3-mercapto-1-(1H-1,2,4-triazol-1-yl)-2-butanol (0.3 g). To the mixture was added dropwise at room temperature a dichloromethane solution (10 ml) of iodine (0.17 g). The mixture was stirred for 30 minutes at room temperature, washed with a 5% aqueous solution of sodium hydrogensulfite and dried ($Na_2SO_4$). The solvent was then distilled off under reduced pressure. The residue was subjected to a silica gel chromatography (2.5×30 cm), eluting with ethyl acetate - hexane (4:1). The objective fraction was concentrated. Addition of diethyl ether-hexane (2:1) to the concentrate gave bis[3-(2,4- difluorophenyl)-3-hydroxy-4-(1H-1,2,4-triazol-1-yl)-2butyl] disulfide (Compound 15, 0.15 g) as a colorless powder.

SIMS m/z (M+H)+: 569

$^1$H-NMR (CDCl$_3$)δ: 1.21–1.28 (6H,m), 3.51–3.67 (2H,m), 5.03–5.12 (6H,m), 6.71–6.81 (4H,m), 7.30–7.48 (2H,m), 7.80 (1H,s), 7.82 (1H,s), 7.84 (1H,s), 7.86 (1H,s)

Example 2

In dichloromethane (10 ml) was dissolved (2R,3R)-2-(2,4-difluorophenyl)-3-mercapto-1-(1H-1,2,4-triazol-1-yl)-2-butanol (143 mg), to which was added dropwise under ice-cooling a dichloromethane solution (10 ml) of iodine (82 mg). The mixture was stirred for 30 minutes at room temperature. The reaction mixture was washed with an aqueous solution of sodium sulfite, then dried over magnesium sulfate. The solvent was distilled off under reduced pressure. The residue was purified by a silica gel chromatography (eluent, hexane - ethyl acetate = 1:3). The objective fraction was concentrated. Addition of hexane to the residue gave bis[(2R,3R)-3-(2,4-difluorophenyl)-3-hydroxy-4-(1H-1,2,4-triazol-1-yl)-2-bu] disulfide (Compound 16, 82 mg) as a colorless powder. mp. 76°–81° C.

$^1$H-NMR (CDCl$_3$)δ: 1.24 (6H,d,J=7.0Hz), 3.60 (2H,q,J=7.0Hz), 5.02 (2H,d,J=1.4Hz), 5.05 (4H,s), 6.68-6.84 (4H,m), 7 30-7.42 (2H,m), 7.79 (2H,s), 7.83 (2H,s)

[α]$_D^{23}$: −78.2° (c=1.0, MeOH)

Example 3

In ethanol (30 ml) was dissolved (2RS,3RS)-2-(2,4-difluorophenyl)-3-mercapto-1-(1H-1,2,4-triazol-1-yl)-2-butanol (0.3 g). To the solution was added sodium S(1,2,3,4-tetrahydrofurfuryl) thiosulfate (0.51 g). To the mixture was added dropwise, with stirring at room temperature, a 1N aqueous solution of sodium hydroxide (1 ml). The mixture was stirred for 30 minutes and then neutralized by the addition of a buffer solution (pH 1.68). The solvent was distilled off under reduced pressure, and the residue was purified by a silica gel column chromatography (4×15 cm, eluent, methylene chloride:acetone=2:1). The objective fraction was concentrated and there was added petroleum ether. The mixture was allowed to stand to give (2RS,3RS)-2-(2,4-difluorophenyl)-3-(1,2,3,4-tetrahydrofurfuryl)dithio-1-(1H-1,2,4-triazol-1-yl)-2-butanol (Compound 1:0.13 g) as colorless powdery crystals.

mp. 46°–50° C.

$^1$H-NMR (CDCl$_3$)δ: 1.20 (3H,d,J=6.8Hz), 1.60-1.80, 1.80-2.20 (4H,m), 2.85-3.10 (2H,m), 3.45-3.62, 3.75-4.00, 4.10-4.25 (4H,m), 4.88-5.05 (3H,m), 6.67-6.71 (2H,m), 7.26-7.42 (1H,m), 7.76 (1H,s), 7.82 (1H,s)

Example 4

To methanol (30 ml) were added (2R,3R)-2-(2,4-difluorophenyl)-3-mercapto-1-(1H-1,2,4-triazol-1-yl)-2-butanol (0.3 g) and sodium S-(2-hydroxyethyl) thiosulfate (0.75 g). To the mixture was added dropwise, under ice-cooling with stirring, a 1N aqueous solution of sodium hydroxide (1 ml). The mixture was stirred for 30 minutes and there were added methylene chloride (50 ml) and water (25 ml). The aqueous layer was made weakly acidic with a buffer solution (pH 1.68). The methylene chloride layer was separated, and the aqueous layer was extracted with methylene chloride (50 ml). Methylene chloride layers were combined, washed with water (30 ml) and dried (MgSO$_4$), followed by distilling off the solvent under reduced pressure. The residue was purified by a silica gel column chromatography (2.9×30 cm, eluent, methylene chloride acetone=1:1). The objective fraction was concentrated to give (2R,3R)-2-(2,4-difluorophenyl)-3-(2-hydroxyethyl)dithio-1-(1H-1,2,4-triazol-1-yl)-2-butanol (Compound 4, 0.24 g) as a colorless oil.

$^1$H-NMR (CDCl$_3$)δ:

1.21 (3H,d,J=7Hz), 2.13 (1H,t,J=6Hz), 2.89-3.09 (2H,m), 3.49 (1H,q,J=7Hz), 3.95 (2H,q,J=6Hz), 4.92-5.08 (3H,m), 6.70-6.79 (2H,m), 7.33-7.41 (1H,m), 7.79 (1H,s), 7.81 (1H,s)

This product (0.24 g) was dissolved in ethyl acetate and treated with a solution of hydrogen chloride in ethyl acetate to give the hydrochloride of Compound 4 as colorless crystals.

Yield 0.075 g m.p. 118°–120° C.

Example 5

In methanol (80 ml) was dissolved (2R,3R)-2-(2,4-difluorophenyl)-3-mercapto-1-(1H-1,2,4-triazol-1-yl)-2-butanol (0.8 g), to which was added sodium S-(1,2,3,4-tetrahydrofurfuryl) thiosulfate (4.5 g). To the mixture was added, under ice-cooling with stirring, a 1N aqueous solution of sodium hydroxide (3 ml). The mixture was stirred for 5 minutes under ice-cooling, then for 120 minutes at room temperature. The reaction mixture was neutralized by the addition of a buffer solution (pH 1.68), then the solvent was distilled off under reduced pressure. The residue was subjected to partition between water (100 ml) and methylene chloride (200 ml). The organic layer was washed with water (100 ml) and dried (MgSO$_4$), followed by distilling off the solvent under reduced pressure. The residue was purified by a silica gel column chromatography (2.9×40 cm, eluent, methylene chloride:acetone=3:1). The objective fraction was concentrated to give (2R,3R)-2-(2,4-difluorophenyl)-3-(1,2,3,4-tetrahydrofurfuryl))dithio-1-(1H-1,2,4-triazol-1-yl)-2-butanol (Compound 2:0.6 g) as a colorless oil.

$^1$H-NMR (CDCl$_3$)δ: 1.20 (3H,d,J=7Hz), 1.60-1.79, 1.80-2.20 (4H,m), 2.85-3.10 (2H,m), 3.46-3.62, 3.74-4.00, 4.09-4.25 (4H,m), 4.88-5.05 (3H,m), 6.68-6.79 (2H,m), 7.26-7.42 (1H,m), 7.77 (1H,s), 7.83 (1H,s)

In ethyl ether (10 ml) was dissolved 0.6 g of this product, to which was added an ethyl acetate solution of hydrogen chloride (1N, 1.6 ml). To the mixture was added petroleum ether (50 ml). The precipitating colorless powder was collected by filtration to obtain Compound 2·hydrochloride (0.5 g).

Example 6

To methanol (30 ml) were added (2R,3R)-2-(2,4-difluorophenyl)-3-mercapto-1-(1H-1,2,4-triazol-1-yl)-2-butanol (0.3 g) and sodium S-(2-acetylaminoethyl) thiosulfate (5.9 g). To the mixture was added dropwise, under ice-cooling with stirring, a 1N aqueous solution of sodium hydroxide (1.5 ml). The mixture was stirred for 5 minutes under ice-cooling, then for 30 minutes at room temperature. To the reaction mixture were added methylene chloride (50 ml) and water (25 ml). The aqueous layer was made weakly acidic with a buffer solution (pH 1.68). The methylene chloride layer was separated out, and the aqueous layer was subjected to extraction with methylene chloride (25 ml). The methylene chloride layers were combined and washed with water (25 ml) and dried (MgSO.), followed by distilling off the solvent under reduced pressure. The residue was purified by a silica gel column chromatography (2.5×40 cm: eluent, ethyl acetate : methanol=15:1). The objective fraction was concentrated to give (2R,3R)-3-(2-acetylaminoethyl)dithio-2-(2,4-difluorophenyl)-1-(1H-1,2,4-triazol-1-yl)-2-butanol (Compound 12 : 0.25 g) as a colorless oil.

$^1$H-NMR (CDCl$_3$)δ: 1.20 (3H,d,J=7Hz), 2.02 (3H,s), 2.87-2.94 (2H,m), 3.48 (1H,q,J=7Hz), 3.59-3.69 (2H,m), 4.97-5.04 (3H,m), 5.93 (1H,bs), 6.69-6.78 (2H,m), 7.32-7.41 (1H,m), 7.77 (1H,s), 7.89 (1H,s)

This product (0.25 g) was added to ethyl ether (20 ml), to which was added an ethyl acetate solution of hydrogen chloride, and the resulting mixture was diluted with petroleum ether (50 ml). The precipitating powder was collected by filtration to obtain Compound 12.hydrochloride (0.21 g) as a colorless powder.

Example 7

Thiamine disulfide (0.59 g) was dissolved in 50% aqueous acetic acid (5 ml), to which was added 30% hydrogen peroxide (0.16 ml). The mixture was allowed to stand overnight and then there was added an ethanol (5 ml) solution of (2RS,3RS)-2-(2,4-difluorophenyl)-3-mercapto-1-(1,2,4-triazol-1-yl)-2-butanol (0.1 g). To the mixture was added dropwise a 20% aqueous solution of sodium hydroxide under ice-cooling. The mixture was adjusted to pH 8 and stirred for 5 hours at room temperature. Ethanol was distilled off under reduced pressure. To the residue was added water (5 ml), followed by extraction twice with ethyl acetate (15 ml). The extract was washed with water (10 ml) and dried (MgSO$_4$). The solvent was distilled off under reduced pressure, and the residue was purified by a silica gel column chromatography (2.0×15 cm, eluent, ethyl acetate:acetone:methanol=2:2:1). The objective fraction was concentrated and then there was added hexane to give Compound 23 (0.032 g) as a colorless powder.

$^1$H-NMR (d$_6$-DMSO)$\delta$: 0.92 (3H,d,J=7.2Hz), 1.99–2.11 (1H,m), 2.04 (3H,s), 2.10–2.29 (1H,m), 2.22 (3H,s), 2.69–2.99 (2H,m), 3.28–3.70 (3H,m), 4.44 (2H,bs), 4.71 (1H,d,J=14.2Hz), 4.87 (1H,d,J=14.2Hz), 6.71 (1H,bs), 6.81–6.96 (1H,m), 7.06–7.28 (2H,m), 7.64 (1H,s), 7.85 (1H,s), 8.00 (1H,s), 8.26 (1H,s)

Example 8

Thiamine disulfide (5.9 g) was dissolved in 50% aqueous acetic acid (50 ml), to which was added 30% hydrogen peroxide (1.6 ml). The mixture was allowed to stand overnight and then there was added an ethanol (50 ml) solution of (2R,3R)-2-(2,4-difluorophenyl)-3-mercapto-1-(1,2,4-triazol-1-yl)-2-butanol (1 g). To the mixture was added dropwise, under ice-cooling, a 20% aqueous solution of sodium hydroxide. The resulting mixture was adjusted to pH 8, and stirred for hours at room temperature. Ethanol was distilled off under reduced pressure. To the residue was added water (50 ml), which was extracted twice with ethyl acetate (100 ml). The extract was washed with water (50 ml) and dried (MgSO$_4$), then the solvent was distilled off under reduced pressure. The residue was purified by a silica gel column chromatography (40×100 cm, eluent, ethyl acetate:acetone:methanol=2:2:1). The objective fraction was concentrated and there was added hexane to obtain Compound 24 (1.3 g) as a colorless powder.

$^1$H-NMR (CDCl$_3$)$\delta$: 1.00 (3H,d,J=6.8Hz), 2.05–2.17 (1H,m), 2.08 (3H,s), 2.40–2.48 (1H,m), 2.41 (3H,s), 2.78–3.06 (2H,m), 3.22 (1H,q,J=6.8Hz), 3.69–3.82 (2H,m), 4.90 (2H,s), 5.16 (1H,s), 6.06 (2H,bs), 6.68–6.85 (2H,m), 7.26–7.39 (1H,m), 7.79 (1H,s), 7.81 (1H,s), 7.83 (1H,s), 8.06 (1H,s)

Example 9

L-N,N'-Diacetylcystine diethyl ester (0.39 g) was dissolved in 50% aqueous acetic acid (5 ml), to which was added a 30% aqueous solution of hydrogen peroxide (0.16 ml). The mixture was allowed to stand overnight and then there was added an ethanol (15 ml) solution of (2RS,3RS)-2-(2,4-difluorophenyl)-3-mercapto-1-(1H-1,2,4-triazol-1-yl)-2-butanol (0.3 g). To the mixture was added dropwise, under ice-cooling, a 20% aqueous solution of sodium hydroxide to adjust the pH at 8, followed by stirring for 90 minutes at room temperature. Ethanol was distilled off under reduced pressure. To the residue was added water (20 ml), which was subjected to extraction with methylene chloride (40 ml). The extract was washed with water (20 ml) and dried (MgSO.), followed by distilling off the solvent under reduced pressure. The residue was purified by a silica gel column chromatography (2.9×100 cm, eluent, ethyl acetate:methanol=50:1). The object fraction was concentrated to give Compound 5 (0.18 g) as a colorless oil.

$^1$H-NMR (CDCl$_3$)$\delta$: 1.16 (3H,d,J=7.2Hz), 1.26–1.36 (3H,m), 2.07 (3H,s), 3.14–3.52 (3H,m), 4.19–4.32 (2H,m), 4.81–5.03 (4H,m), 6.39 (1H,d,J=6.2Hz), 6.70–6.81 (2H,m), 7.31–7.42 (1H,m), 7.77 (1H), 7.86 (1H) .

Example 10

Ethoxycarbonylsulfenyl chloride (0.12 g) was dissolved in ethanol (2 ml). To the solution was added portionwise at room temperature (2RS,3RS)-2-(2,4-difluorophenyl)-3-mercapto-1-(1H-1,2,4-triazol-1-yl)-2-butanol (0.22 g). The reaction mixture was stirred for 5 minutes at room temperature, then the solvent was distilled off under reduced pressure. To the residue was added diethyl ether to give ethyl [(2RS,3RS)-3-(2,4-difluorophenyl)-3-hydroxy-4-(1H-1,2,4-triazol-1-yl)-2-butyl]dithiocarbonate hydrochloride (Compound 21:0.25 g) as a colorless powder.

$^1$H-NMR (CDCl$_3$)$\delta$: 1.21 (3H,d,J=6.8Hz), 1.38 (3H,t,J=7.2Hz), 3.73 (1H,q,J=6.8Hz), 4.42 (2H,q,J=7.2Hz), 5.13 (2H,d,J=14.4Hz), 5.60 (2H,d,J=14.4Hz), 6.70–6.90 (2H,m), 7.28–7.46 (1H,m), 8.15 (1H,s), 10.07 (1H,s)

Example 11

Ethoxycarbonylsulfenyl chloride (1.18 g) was dissolved in ethanol (20 ml). To the solution was added portionwise under ice-cooling (2R,3R)-2-(2,4-difluorophenyl)-3-mercapto-1-(1H-1,2,4-triazol-1-yl)-2-butanol (2.0 g). The reaction mixture was stirred for 30 minutes at room temperature, then the solvent was distilled off under reduced pressure. The residue was dissolved in ethyl acetate. The solution was washed with an aqueous solution of sodium hydrogencarbonate and then with a saturated aqueous solution of sodium chloride, followed by drying over magnesium sulfate. The solvent was distilled off under reduced pressure to give ethyl [(2R,3R)-3-(2,4-difluorophenyl)-3-hydroxy-4-(1H-1,2,4-triazol-1-yl)-2-butyl]dithiocarbonate (Compound 22:2.60 g) as a colorless oil.

$^1$H-NMR (CDCl$_3$)$\delta$: 1.20 (3H,d,J=6.8Hz), 1.38 (3H,t,J=7.2Hz), 3.53 (1H,q,J=6.8Hz), 4.41 (2H,q,J=7.2Hz), 4.97 (2H,d,J=14.4Hz), 5.12 (1H,s,OH), 5.28 (2H,d,J=14.4Hz), 6.68–6.82 (2H,m), 7.26–7.42 (1H,m), 7.77 (1H,s), 7.86 (1H,s)

Example 12

L-N,N'-Diacetylcystine diethyl ester (0.93 g) was dissolved in 50% aqueous acetic acid (12 ml). To the solution was added 30% hydrogen peroxide (0.41 ml), which was allowed to stand overnight. To the mixture was added a solution of (2R,3R)-2-(2,4-difluorophenyl)-3-mercapto-1-(1H-1,2,4-triazol-1-yl)-2-butanol (0.7 g) in ethanol (25 ml). To the mixture was added dropwise, under ice-cooling, a 20% aqueous solution of sodium hydroxide to adjust the pH of the reaction mixture at 8, followed by stirring for 90 minutes at room temperature. Ethanol was distilled off under reduced pressure. To the residue was added water (20 ml), which was subjected to extraction with methylene chloride (50 ml). The extract was washed with water (20 ml) and dried (MgSO$_4$), followed by distilling off the solvent under reduced pressure. The residue was purified by a silica gel column chromatography (50×100 cm, eluent, ethyl acetate:methanol=50:1). The objective fraction was concentrated to give Compound 6 (0.45 g) as a colorless oil.

$^1$H-NMR (CDCl$_3$)δ: 1.20 (3H,d,J=7.2Hz), 1.32 (3H,t,J=7Hz), 2.08 (3H,s), 3.20–3.39 (2H,m), 3.49 (1H,q,J=7.2Hz), 4.28 (2H,q,J=7Hz), 4.89–5.06 (4H,m), 6.37 (1H,d,J=8Hz), 6.70–6.79 (2H,m), 7.33–7.42 (1H,m), 7.77 (1H,s), 7.87 (1H,s)

This product (0.45 g) was dissolved in ethyl acetate and treated with 2N solution of hydrogen chloride in ethyl acetate to give the hydrochloride of Compound 6 as a colorless powder (0.37 g).

Elemental Analysis for C$_{19}$H$_{24}$F$_2$N$_4$O$_4$S$_2$·HCl: Calcd.: C, 44.66; H, 4.93; N, 10.96. Found: C, 44.64; H, 4.95; N, 10.73.

SIMS(m/z): 475(M+H)$^+$

Example 13

In methanol (50 ml) were dissolved (2R,3R)-2-(2,4-difluorophenyl)-3-mercapto-1-(1H-1,2,4-triazol-1-yl)-2-butanol (0.5 g) and sodium S-(2,3-dihydroxypropyl) thiosulfate (5.5 g). To the stirred solution was added dropwise under ice-cooling 1N aqueous solution of sodium hydroxide (1.75 ml). The mixture was stirred for one hour and then there were added methylene chloride (50 ml) and water (50 ml). The aqueous layer was neutralized with 1N hydrochloric acid. The methylene chloride layer was separated, and the aqueous layer was extracted with methylene chloride (25 ml). The methylene chloride layers were combined and washed with water (50 ml), followed by drying (MgSO$_4$). The solvent was distilled off under reduced pressure. The residue was purified by a silica gel column chromatography (2.9×50 cm, eluent, ethyl acetate: methanol=15:1 - 9:1). The objective fraction was concentrated to obtain Compound 10 (0.21 g) as a colorless oil.

$^1$H-NMR (CDCl$_3$)δ: 1.19–1.25 (3H,m), 2.07–2.20 (1H,m), 2.74–3.09 (3H,m), 3.47–4.07 (4H,m), 4.98–5.04 (3H,m), 6.71–6.81 (2H,m), 7.31–7.42 (1H,m), 7.79–7.81 (2H,m)

This product (0.2 g) was dissolved, in ethyl acetate and treated with 2N solution of hydrogen chloride in ethyl acetate to give the hydrochloride of Compound 10 as a colorless powder (0.17 g).

Elemental Analysis for C$_{15}$H$_{19}$F$_2$N$_3$O$_3$S$_2$·HCl·½H$_2$O: Calcd.: C, 41.23; H, 4.84; N, 9.62. Found: C, 41.02; H, 4.61; N, 9.81.

Example 14

In dichloromethane (15 ml) was dissolved (2R,3R)-2-(2,4-di fluorophenyl)-3-mercapto-1-(1H-1,2,4-triazol-1-yl)-2-butanol (0.5 g). To the solution was added, under ice-cooling, triethylamine (0.27 ml), followed by addition of methanesulfonyl chloride (0.27 ml). The mixture was stirred for 30 minutes at room temperature and then there was added water (10 ml), followed by extraction with dichloromethane (20 ml). The extract was washed with water (10 ml) and dried (MgSO$_4$), followed by distilling off the solvent under reduced pressure. The residue was purified by a silica gel column chromatography (2.9×30 cm, eluent, ethyl acetate) to obtain Compound 16 (0.25 g) as a colorless powder.

$^1$H-NMR (CDCl$_3$)δ: 1.24 (6H,d,J=7Hz), 3.60 (2H,q,J=7Hz), 5.06 (4H,s), 5.08 (2H,s), 6.68–6.84 (4H,m), 7.30–7.42 (2H,m), 7.79 (2H,s), 7.85 (2H,s)

Example 15

In methanol (6 ml) were dissolved [(2R,3R)-3-(2,4-difluorophenyl)-3-hydroxy-4-(1H-1,2,4-triazol-1-yl)-2butyl] ethoxycarbonyl disulfide (Compound 22 : 0.30 g) and L-cystine hydrochloride monohydrate (0.15 g). To the solution was added triethylamine (85 μl), and the mixture was stirred for one hour at room temperature. To the reaction mixture was added 1N (1 ml), then the insoluble substance was were filtered off, and the filtrate was concentrated. The concentrate was subjected to a reversed phase (ODS) liquid chromatography (eluent, methanol-water=2:1) for purification. The objective fraction was concentrated under reduced pressure, followed by recrystallization from methanol-water to give Compound 18 (0.13 g) as a colorless crystalline powder.

SIMS (m/z): 405 (M+H)$^+$

IR($\nu_{max}^{KBr}$cm$^{-1}$):3420, 1615, 1500, 1382, 1270, 1135

NMR (DMSO-d$_6$+D$_2$O)δ: 1.12 (3H,d,J=7Hz), 3.20–3.25 (2H,m), 3.60 (1H,q,J=7Hz), 3.71 (1H,m), 4.79 (1H,d,J=14Hz), 4.96 (1H,d,J=14Hz), 6.89 (1H,m), 7.08–7.32 (2H,m), 7.63 (1H,s), 8.42 (1H,s)

Example 16

In methanol (6 ml) was dissolved [(2R,3R)-3-(2,4-difluorophenyl)-3-hydroxy-4-(1H-1,2,4-triazol-1-yl)-2-butyl] ethoxycarbonyl disulfide (Compound 22: 0.30 g). To the solution was added 2-dimethylaminoethanethiol hydrochloride (0.13 g), and the mixture was stirred for 30 minutes at room temperature. Methanol was distilled off under reduced pressure. The residue was purified by a silica gel column chromatography (eluent, ethyl acetate - methanol=2:1). The objective fraction was concentrated and there was added 4N-HCl (ethyl acetate solution : 0.4 ml). Then separating precipitates were collected by filtration and washed-with diethyl ether to give Compound 28 dihydrochloride (187 mg) as a colorless powder.

IR($\nu_{max}^{KBr}$cm$^{-1}$):3400, 1620, 1505, 1420, 1275, 1135

NMR (DMSO-d$_6$)δ: 1.17 (3H,d,J=7Hz), 2.80 (6H,d,J=4.8Hz), 3.13–3.48 (4H,m), 3.62 (1H,q,J=7Hz), 4.91 (2H,s), 6.94 (1H,m), 7.10–7.32 (2H,m), 7.79 (1H,s), 8.49 (1H,s)

SIMS (m/z): 389 (M+H)$^+$

Example 17

In methanol (10 ml) were dissolved [(2R,3R)-3-(2,4difluorophenyl)-3-hydroxy-4-(1H-1,2,4-triazol-1-yl)-2)-butyl] ethoxycarbonyl disulfide (Compound 22:0.50 g) and glutathione (reduced, 474 mg). To the solution was added dropwise, under ice-cooling, triethylamine (0.43 ml). The reaction mixture was stirred for 30 minutes at room temperatures and then there was added 1N-HCl (3 ml). The insoluble substance was filtered off, and the filtrate was concentrated under reduced pressure. The concentrate was washed with ethyl acetate. The powdery product thus obtained was purified by a reversed phase (ODS) liquid chromatography (eluent:methanol-water=2:1). The objective fraction was concentrated under reduced pressure to give Compound 34 (0.20 g) as a colorless powder.

IR($\nu_{max}^{KBr}$cm$^{-1}$):3400, 1738, 1650, 1500, 1410, 1270, 1130

NMR (DMSO-d$_6$+D$_2$O)δ: 1.13 (3H,d,J=7Hz), 1.90 (2H,m), 2.37 (2H,m), 2.85-3.40 (4H,m), 3.51 (1H,q,J=7Hz), 3.69 (1H,d,J=5Hz), 4.61 (1H,m), 4.78 (1H,d,J=14Hz), 4.95 (1H,d,J=14Hz), 6.89 (1H,m), 7.06-7.30 (2H,m), 7.65 (1H,s), 8.32 (1H,s)

SIMS (m/z): 591 (M+H)+

Example 18

In methanol (6 ml) were dispersed [(2R,3R)-3-(2,4-difluorophenyl)-3-hydroxy-4-(1H-1,2,4-triazol-1-yl)-2-butyl] ethoxycarbonyl disulfide (Compound 22: 0.30 g) and D-penicillamine (138 mg). To the dispersion was added one drop of triethylamine, and the mixture was stirred for one hour at room temperature. The solvent was distilled off under reduced pressure, and the residue was washed with ethyl acetate and ether. The methanol-soluble portion of the residue was purified by a reversed phase (ODS) liquid chromatography (eluent, methanol-water=2:1). The objective fraction was concentrated to give Compound 36 (0.13 g) as a colorless powder.

IR($\nu_{max}^{KBr}$cm$^{-1}$):3380, 1610, 1485, 1380, 1270, 1130

NMR (DMSO-d$_6$)δ: 1.08 (3H,d,J=7Hz), 1.35 (3H,s), 1.51 (3H,s), 3.37 (1H,s), 3.61 (1H,q,J=7Hz), 4.87 (1H,d,J=14Hz), 4.98 (1H,d,J=14Hz), 6.89 (1H,m), 7.10-7.28 (2H,m), 7.63 (1H,s), 8.34 (1H,s)

Example 19

In dichloromethane (6 ml) was dissolved bis[(2R,3R)-3-(2,4-di fluorophenyl)-3-hydroxy-4-(1H-1,2,4-triazol-1-yl)-2-butyl] disulfide (Compound 16: 0.24 g). To the solution was added dropwise, under ice-cooling, a dichloromethane solution (1 ml) of m-chloroperbenzoic acid (85 mg). The mixture was stirred for 20 minutes under ice-cooling. The reaction mixture was concentrated under reduced pressure. The concentrate was purified by a flash chromatography using silica gel (eluent, dichloromethane - ethyl acetate - methanol =5:1). The objective fraction was concentrated, to which was added diethyl ether to give Compound 31 (89 mg) as a colorless powder.

IR($\nu_{max}^{KBr}$cm$^{-1}$):1615, 1500, 1420, 1270, 1135

NMR (CDCCl$_3$)δ: 1.17-1.45 (6H,m), 3.85-4.20 (2H,m), 4.80-5.65 (6H,m), 6.70-6.88 (4H,m), 7.30-7.52 (2H,m), 7.74(1H,s), 7.80 (1H,s), 7.89 (1H,s), 7.93 (1H,s)

SIMS (m/z) 585 (M+H)+

Example 20

In dichloromethane (4 ml) was dissolved bis[(2R,3R)-3-(2,4-difluorophenyl)-3-hydroxy-4-(1H-1,2,4-triazol-1-yl)-2-butyl] disulfide (Compound 16: 200 mg). To the solution was added, under ice-cooling, m-chloroperbenzoic acid (142 mg). The reaction mixture was stirred for two hours at room temperatures, washed with a 5% aqueous solution of sodium hydrogencarbonate, dried (magnesium sulfate) and, then, concentrated. The concentrate was purified by a flash chromatography using silica gel (eluent, dichloromethane - ethyl acetate - methanol =5:5:1). The objective fraction was concentrated to give Compound 32 (48 mg) as a colorless powder.

IR($\nu_{max}^{KBr}$cm$^{-1}$):3400, 1615, 1500, 1420, 1310, 1270, 1130

NMR (CDCl$_3$)δ: 1.37 (3H,d,J=7Hz), 1.38 (3H,d,J=7Hz), 4.09 (1H,q,J=7Hz), 4.30 (1H,dd,J=7Hz,J=1.4Hz), 4.92-5.15 (3H,m), 5.35-5.50 (3H,m), 6.68-6.88 (4H,m), 7.23-7.45 (2H,m), 7.76 (1H,s), 7.80 (1H,s), 7.82 (1H,s), 7.83 (1H,s)

SIMS (m/z): 601 (M+H)+

Example 21

In methanol (20 ml) was dissolved [(2R,3R)-3-(2,4-difluorophenyl-3-hydroxy-4-(1H-1,2,4-triazol-1-yl)-2-butyl] ethoxycarbonyl disulfide (Compound 22: 2.2 g). To the solution was added dropwise at −78° C. a methanol solution (2 ml) of potassium tert-butoxide (0.56 g). The reaction mixture was stirred for 5 minutes at 0° C., to which was added acetic acid (0.3 ml), followed by concentration under reduced pressure. The concentrate was purified by a liquid chromatography using a reversed phase (ODS) column (eluent, methanol-water=8:2). The objective fraction was concentrated to give Compound 29 (0.87 g) as a colorless powder.

IR($\nu_{max}^{KBr}$cm$^{-1}$):3400, 1620, 1505, 1424, 1270, 1138, 1045

NMR (CDCl$_3$)δ: 1.30 (6H,d,J=7Hz), 3.74 (2H,q,J=7Hz), 4.99 (6H,s), 6.71-6.85 (4H,m), 7.27-7.43 (2H,m), 7.78 (2H,s), 7.80 (2H,s)

SIMS (m/z): 601 (M+H)+

Example 22

In methanol (10 ml) was dissolved [(2R,3R)-3-(2,4-difluorophenyl)-3-hydroxy-4-(1H-1,2,4-triazol-1-yl)-2-butyl] ethoxycarbonyl disulfide (Compound 22 : 0.60 g). To the solution was added, under ice-cooling, a methanol solution (1 ml) of potassium tert-butoxide (0.166 g). The reaction mixture was stirred for 15 minutes at room temperature and then there was added 1N-HCl (1.5 ml). The reaction mixture was concentrated under reduced pressure. The concentrate was purified by a liquid chromatography using ODS column to give Compound 30 (23 mg) as a colorless powder.

IR($\nu_{max}^{KBr}$cm$^{-1}$):3420, 1620, 1505, 1420, 1275, 1140

NMR (CDCl$_3$)δ: 1.31 (6H,d,J=7Hz), 3.82 (2H,q,J=7Hz), 5.02 (2H,s), 5.04 (2H,s), 5.14 (2H,d,J=1.6Hz), 6.65-6.84 (4H,m), 7.25-7.45 (2H,m), 7.81 (1H,s), 7.82 (2H,s)

SIMS (m/z): 633 (M+H)+

Example 23

In methanol (6 ml) were dissolved [(2R,3R)-3-(2,4-difluorophenyl)-3-hydroxy-4-(1H-1,2,4-triazol-1-yl)-2-butyl] ethoxycarbonyl disulfide (0.30 g) and N-acetyl-L-cysteine (0.18 g). To the solution was added triethylamine (0.15 ml), and the mixture was stirred for 30 minutes at room temperature. The reaction mixture was concentrated under reduced pressure. The concentrate was purified by a silica gel chromatography (eluent, chloroform-methanol-water=65:25:4). The objective fraction was concentrated under reduced pressure. Addition of diethyl ether to the concentrate gave Compound 8 (0.22 g) as a colorless powder.

IR($\nu_{max}^{KBr}$cm$^{-1}$):3400, 1650, 1615, 1500, 1420, 1270, 1138

NMR (CDCl$_3$)δ: 1.08 (3H,d,J=7Hz), 1.89 (3H,s), 2.60-3.80 (3H,m), 4.26-4.40 (1H,m), 4.77 (1H,d,J=14Hz), 4.97 (1H,d,J=14Hz), 6.80 (1H,m), 7.05-7.35 (2H,m), 7.61 (1H,s), 8.44 (1H,s)

SIMS (m/z) 447 (M+H)+

Example 24

[(2R,3R)-3-(2,4-difluorophenyl)-3-hydroxy-4-(1H-1,2,4-triazol-1-yl)-2-butyl]ethoxycarbonyl disulfide hydrochloride (Compound 22 hydrochloride:0.64 g) was dissolved in aqueous ethanol (ethanol 20 ml and water 15 ml). To the solution was added sodium diethyldithiocarbamate (1.35 g), and the mixture was stirred for one hour at room temperature. The reaction mixture was subjected to partition between dichloromethane (50 ml) and water (15 ml). The aqueous layer was extracted with dichloromethane (20 ml). The dichloromethane layers were combined and washed with water (20 ml) and then dried ($MgSO_4$). The solvent was distilled off under reduced pressure. The residue was purified by a silica gel chromatography (2.9×30 cm, eluent:hexane-ethyl acetate=3:1ethyl acetate). The objective fraction was concentrated, and the concentrate was treated with a solution of hydrogen chloride in ethyl acetate to give Compound 39 (0.41 g), as the hydrochloride, m.p. 108°–109° C.

Elemental Analysis for $C_{17}H_{22}F_2N_4OS_3HCl$: Calcd.: C,43.53; H,4.94; N,11.94. Found : C,43.39; H,4.95; N,11.71.

NMR($d_6$-DMSO)δ: 1.12(3H,d,J=7Hz), 1.17–1.33(6H,m), 3.62–4.08 (5H,m), 4.95(1H,d,J=14Hz), 5.35(1H,d,J=14Hz), 6.83–6.97(1H,m), 7.09–7.27(2H,m), 7.94(1H,s), 8.79(1H,s)

Example 25

[(2R,3R)-3-(2,4-difluorophenyl)-3-hydroxy-4-(1H-1,2,4-triazol-1-yl)-2-butyl] ethoxycarbonyl disulfide hydrochloride (Compound 22 hydrochloride:0.64 g) and 2-mercaptomethyl-1-methylimidazole (0.29 g) were dissolved in ethanol (20 ml), to which was added triethylamine (0.22 ml). The mixture was stirred for one hour at room temperature. The solvent was distilled off under reduced pressure. To the residue was added water (50 ml), which was subjected to extraction with ethyl acetate (50 ml ×2). The extract was washed with water (30 ml) and dried ($MgSO_4$). The solvent was distilled off under reduced pressure. The residue was purified by a silica gel chromatography (2.9×30 cm, eluent : dichloromethane-acetone=1:1). The objective fraction was concentrated and there was added diisopropyl ether to give Compound 40 (0.19 g) as colorless needles, m.p. 112°–113° C.

Elemental Analysis for $C_{17}H_{19}F_2N_5OS_2$: Calcd.: C,49.62; H,4.65; N,17.02. Found : C,49.51; H,4.74; N,17.08.

NMR($CDCl_3$)δ: 1.13(3H,d,J=6.8Hz), 3.53(1H,q,J=6.8Hz), 3.73(3H,s), 3.84(1H,d,J=14Hz), 4.18(1H,d,J=14Hz), 4.77(1H,d,J=14.4Hz), 4.99(1H,d,J=14.4Hz), 6.68–6.82 (2H,m), 6.96(1H,s), 7.03(1H,s), 7.40–7.53 (2H,m), 7.70(1H,s), 8.15(1H,s)

Example 26

[(2R,3R)-3-(2,4-difluorophenyl)-3-hydroxy-4-(1H-1,2,4-triazol-1-yl)-2-butyl] ethoxycarbonyl disulfide hydrochloride (212 mg) was dissolved in ethanol (5 ml), to which was added an aqueous solution (2 ml) of 2-mercaptopropionyl glycine sodium salt (100 mg). The mixture was stirred for two hours at room temperature, then the reaction mixture was concentrated. The concentrate was purified by chromatography (eluent: methanol-water=8:2) using CHP-20 resin (manufactured by Mitsubishi Chemical Industries, Ltd.). The objective fraction was concentrated and there was added diethyl ether to afford Compound 41 (145 mg) as a white powder.

$^1$H-NMR(DMSO-$d_6$+$D_2O$)δ: 1.08(3H,d,J=6.6Hz), 1.42(3H,d,J=6.8Hz), 3.55–4.10 (5H,m), 4.80(1H,d,J=14Hz), 4.96(1H,d,J=14Hz), 6.80–6.95(1H,m), 7.00–7.30(2H,m), 7.65(1H,s), 8.29(1H,s)

IR(KBr): 3400, 1720, 1650, 1615, 1500, 1275, 1138 $cm^{-1}$

Example 27

To a dichloromethane (20 ml) solution of 1-(2,4-difluorophenyl)-1-[1-(1-mercaptocyclopropyl)] ᵀᴹ 2-(1H-1,2,4-triazol-1-yl)ethanol (0.5 g) and triethylamine (0.47 ml) was added dropwise, under ice-cooling, a dichloromethane solution of iodine (0.213 g) over the period of 15 minutes. The mixture was stirred for 45 minutes at room temperature and there was then added dichloromethane (30 ml). The reaction mixture was washed with water (15 ml) and then with a 10% aqueous solution of sodium hydrogensulfite (25 ml). The dichloromethane layer was dried ($MgSO_4$), then the solvent was distilled off. The residue was purified by a silica gel chromatography (2.9×20 cm, eluent, ethyl acetate:methanol=40:1). The object fraction was concentrated and there was added hexane to give Compound 42 (0.4 g) as a white powder. $^1$H-NMR($CDCl_3$)δ: 1.02–1.34(8H,m), 4.54–4.68(2H,m), 5.18–5.28(2H,m), 5.57(2H,s), 6.63–6.83(4H,m), 7.46–7.58(2H,m), 7.73(2H,s), 8.08(1H,s), 8.09(1H,s)

Example 28

To a dichloromethane (20 ml) solution of 2-(2,4-difluorophenyl)-3-mercapto-3-methyl-1-(1H-1,2,4-triazol-1-yl)-2-butanol (0.3 g) and triethylamine (0.28 ml) was added dropwise, under ice-cooling, a dichloromethane solution of iodine (0.127 g) over the period of 15 minutes. The mixture was stirred for 15 minutes at room temperature. To the reaction mixture was then added dichloromethane (30 ml). The reaction mixture was washed with water (15 ml) and a 10% aqueous solution of sodium hydrogensulfite (20 ml), successively. The dichloromethane layer was dried ($MgSO_4$), then the solvent was distilled off under reduced pressure. The residue was purified by a silica gel chromatography (2.9×15 cm, eluent, ethyl acetate). The objective fraction was concentrated, to which was added diethyl ether to give Compound 43 (0.2 g) as a white powder.

$^1$H-NMR($CDCl_3$)δ: 1.34–1.39(12H,m), 4.73–4.84(2H,m), 5.28–5.35 (2H,m), 5.47(2H,s), 6.59–6.85(4H,m), 7.59–7.62 (2H,m), 7.74(2H,s), 8.07(1H,s), 8.08(1H,s)

Elemental Analysis for $C_{26}H_{28}F_4N_6O_2S_2$: Calcd.: C,52.34; H,4.73; N,14.08. Found : C,52.34; H,4.81; N,13.73.

Example 29

To a solution of (2R,3R)-2-(2,4-difluorophenyl)-1-(1-imidazolyl)-3-mercapto-2-butanol (0.51 g) in methylene chloride (30 ml) was added sodium hydrogencarbonate (1.0 g) at 0 C. To the mixture was then added a solution of iodine (0.23 g) in methylene chloride (30 ml) over the period of 8 minutes. After stirring for seven minutes, the reaction mixture was subjected to extraction by the addition of water (20 ml) and ethyl acetate (50 ml). The aqueous layer was further extracted with ethyl acetate (30 ml). The ethyl acetate layers were combined, washed with a saturated aqueous solution of sodium chloride (10 ml) and dried over anhydrous magnesium sulfate and then concentrated under reduced pressure. The concentrate was subjected to a silica gel chromatography (3 cm × 10 cm), eluting with methylene chloride - methanol (9:1). The objective fraction was concentrated under reduced pressure. To the concentrate were added methanol, methylene chloride and diethyl ether to give a disulfide derivative (Compound 44) as a white powder (0.48 g).

m.p. 125° to 135° C.

$^1$H-NMR(DMSO-d$_6$)δ: 1.20(6H,d,J=6.8Hz), 3.61(2H,q,J=6.8Hz), 4.56(2H,d,J=14.4Hz), 4.74(2H,d,J=14.4Hz), 6.21(2H,s), 6.68(2H,s), 6.82(2H,s), 6.91-7.00(2H,m), 7.16-7.31(4H,m), 7.36(2H,s)

Elemental Analysis for $C_{26}H_{26}F_4N_4O_2S_2H_2O$: Calcd.: C,51.82; H,5.02; N,9.30. Found : C,51.49; H,4.78; N,8.93.

$[α]_D^{25} = -49.1°$ (C=1.2, in methanol)

IR(KBr) cm$^{-1}$: 3100, 1610, 1500, 1420, 1110

What we claim:

1. A compound of the formula:

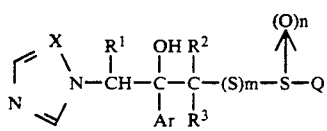

wherein Ar stands for a phenyl having 1 to 3 substituents independently selected from halogen and trifluoromethyl; $R^1$, $R^2$ and $R^3$ independently stand for a hydrogen atom or a lower alkyl group; Q stands for a group represented by the formula:

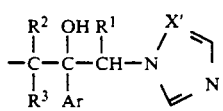

wherein Ar, $R^1$, $R^2$ and $R^3$ are of the same meaning as defined above; X' is a CH group or a nitrogen atom; X stands for a nitrogen atom; m denotes an integer of 1 to 4; n denotes an integer of 0 to 2, or a physiologically acceptable salt thereof.

2. A compound according to claim 1, wherein Ar is 2,4-difluorophenyl.

3. A compound according to claim 1, wherein $R^1$ is a hydrogen atom.

4. A compound according to claim 1, wherein $R^2$ and $R^3$ are the same or different and represent a hydrogen atom or a methyl group.

5. A compound according to claim 1, wherein $R^1$ and $R^2$ are hydrogen atoms, $R^3$ is a methyl group.

6. A compound according to claim 5, wherein both the carbon bonded to hydroxyl and Ar groups and the carbon bonded to $R^2$ are of R-configuration.

7. A compound according to claim 1, wherein the integral number m is 1.

8. A compound according to claim 1, wherein the integral number n is 0.

9. A compound according to claim 1, wherein X' is a nitrogen atom.

10. A compound according to claim 1, wherein Ar is 2,4-difluorophenyl.

11. A compound according to claim 1, wherein $R^1$ is a hydrogen atom.

12. A compound according to claim 1, wherein $R^2$ and $R^3$ are the same or different and represent a hydrogen atom or a methyl group.

13. A compound according to claim 1, wherein $R^1$ and $R^2$ are hydrogen atoms, $R^3$ is a methyl group.

14. A compound according to claim 19, wherein both the carbon bonded to hydroxyl and Ar groups and the carbon bonded to hydroxyl and Ar groups and the carbon bonded to $R^3$ are of R-configuration.

15. A compound according to claim 1, wherein the integral number m is 1.

16. A compound according to claim 1, wherein the integral number n is 0.

17. A compound according to claim 1, wherein the compound is Bis[(2R,3R)-3-(2,4-difluorophenyl)-3-hydroxy-4-(1H-1,2,4-triazol-1-yl)-2-butyl] disulfide.

18. An antifungal composition which contains an effective amount of a compound of the formula:

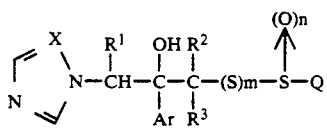

wherein Ar stands for a phenyl having 1 to 3 substituents independently selected from halogen and trifluoromethyl; $R^1$, $R^2$ and $R^3$ independently stand for a hydrogen atom or a lower alkyl group; Q stands for a group represented by the formula:

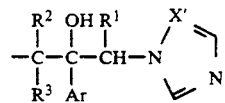

wherein Ar, $R^1$, $R^2$ and $R^3$ are of the same meaning as defined above; X' is a CH group or a nitrogen atom; X stands for a nitrogen atom; m denotes an integer of 1 to 4; n denotes an integer of 0 to 2, or a pharmacologically acceptable salt thereof, and a pharmacologically acceptable carrier.

19. An antifungal composition according to claim 18, wherein Ar is 2,4-difluorophenyl.

20. An antifungal composition according to claim 18, wherein X' is a nitrogen atom.

21. An antifungal composition according to claim 20, wherein Ar is 2,4-difluorophenyl.

22. An antifungal composition according to claim 18, wherein the compound is Bis-[(2R,3R)-3-(2,4-difluorophenyl)-3-hydroxy-4-(1H-1,2,4-triazol-1-yl)-2-butyl] disulfide.

* * * * *